(12) United States Patent
Iwasaki et al.

(10) Patent No.: US 6,503,193 B1
(45) Date of Patent: Jan. 7, 2003

(54) FLEXIBLE TUBE FOR ENDOSCOPE

(75) Inventors: Tomoko Iwasaki, Chiba-ken (JP);
Kenichi Ohara, Gunma-ken (JP);
Akira Sugiyama, Kanagawa-ken (JP);
Naoya Ouchi, Saitama-ken (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 09/548,676

(22) Filed: Apr. 13, 2000

(30) Foreign Application Priority Data

Apr. 14, 1999 (JP) .......................................... 11-106291

(51) Int. Cl.⁷ ................................................ A61B 1/00
(52) U.S. Cl. ...................................... 600/140; 600/139
(58) Field of Search ............................... 600/140, 139, 600/133, 143

(56) References Cited

U.S. PATENT DOCUMENTS

| | | | | |
|---|---|---|---|---|
| 4,327,711 A | * | 5/1982 | Takagi ........................ 600/139 |
| 4,790,831 A | * | 12/1988 | Skribiski ..................... 604/264 |
| 4,944,287 A | * | 7/1990 | Takahashi et al. ........... 420/401 |
| 5,058,567 A | * | 10/1991 | Takahashi et al. ........... 420/401 |
| 5,279,280 A | * | 1/1994 | Bacich et al. ................ 600/104 |
| 5,394,864 A | * | 3/1995 | Kobayashi et al. .......... 138/124 |
| 5,465,710 A | * | 11/1995 | Miyagi et al. ............... 138/123 |
| 6,004,639 A | * | 12/1999 | Quigley et al. .............. 138/125 |
| 6,017,335 A | * | 1/2000 | Burnham ..................... 138/123 |
| 6,206,824 B1 | * | 3/2001 | Ohara et al. ................. 600/139 |

* cited by examiner

Primary Examiner—Linda C. M. Dvorak
Assistant Examiner—Jocelyn Ram
(74) Attorney, Agent, or Firm—Greenblum & Bernstein, P.L.C.

(57) ABSTRACT

A flexible tube for an endoscope is provided with an outer tube member. A synthetic resin layer is formed on an outer circumferential surface of the outer tube member. A coating layer is further formed on the outer circumferential surface of the synthetic resin layer. The outer circumferential surface of the synthetic resin layer is provided with at least one groove or protrusion.

24 Claims, 4 Drawing Sheets

FLEXIBLE TUBE FOR ENDOSCOPE

BACKGROUND OF THE INVENTION

The present invention relates to a flexible tube for an endoscope.

A flexible tube for an endoscope is generally formed as follows.

1. Belt-like material made of metal or synthetic resin is wound in a spiral fashion at a predetermined diameter to form a spirally-wound tube.
2. Thus formed spirally-wound tube is covered with a braided wire tube which is formed by braiding thin wires.
3. Further, the braided wire tube is coated, on its outer surface, with a sheath (or a layer) made of synthetic resin.

The flexible tube is disinfected with a strong disinfectant after it is used. Therefore, recently, in order to prevent deterioration of the synthetic resin layer by the disinfectant, a coating layer of chemical resistant agent is formed on the outer surface of the synthetic resin.

The coating layer is formed in accordance with a vacuum evaporation on a smoothly finished circumferential surface of the synthetic resin layer. However, such a coating layer is not so adhesive with respect to the synthetic resin. Therefore, the coating layer is gradually removed during usage, and the synthetic resin layer is exposed to outside. In such a situation, if the flexible tube is repeatedly disinfected with using the strong disinfectant, the synthetic resin will be deteriorated.

SUMMARY OF THE INVENTION

It is therefore an object of the present invention to provide an improved flexible tube in which the coating layer is difficult to be removed from the synthetic resin layer, and has an excellent property of resistance against the disinfectant.

For the above object, according to a present invention, there is provided a flexible tube for an endoscope, having an outer tube member, a synthetic resin layer being formed on an outer circumferential surface of the outer tube member, a coating layer being formed on the outer circumferential surface of the synthetic resin layer, the outer circumferential surface of the synthetic resin layer being provided with at least one groove or protrusion.

Optionally and preferably, the at least one groove or the protrusion may be provided over substantially an entire length of the flexible tube.

Further optionally, the at least one groove or protrusion extends substantially parallel with an axis of the outer tube member.

The outer tube member may be formed with a plurality of grooves and/or protrusions.

Further optionally, the at least one groove or protrusion may be formed helically on a circumferential surface of the synthetic resin layer.

BRIEF DESCRIPTION OF THE ACCOMPANYING DRAWINGS

FIG. 1 schematically shows an appearance of an endoscope to which the invention is applied;

DETAILED DESCRIPTION OF THE EMBODIMENTS

Hereinafter, embodiments of the present invention will be described with reference to the accompanying drawings.

Figure 1:
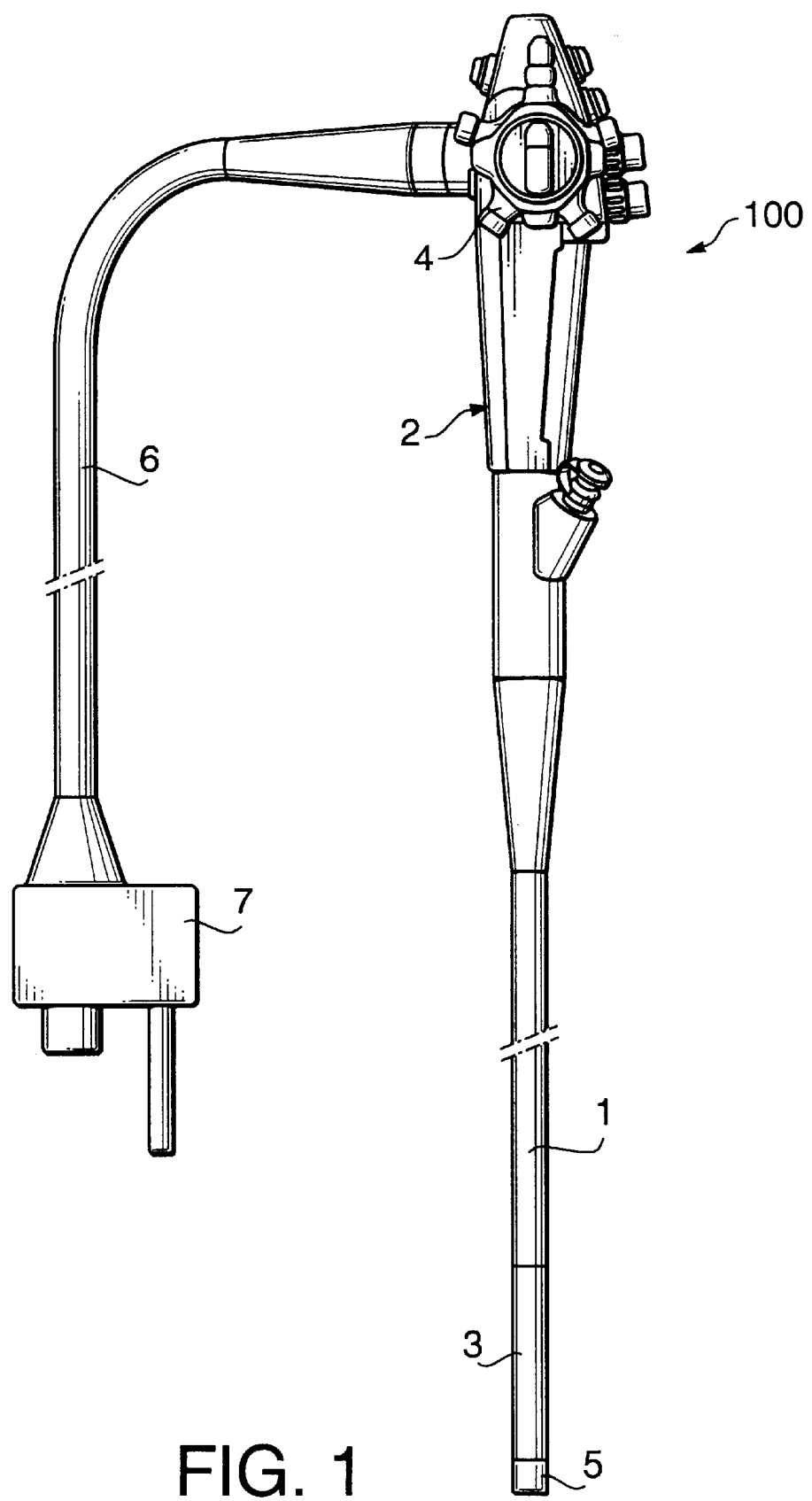

FIG. 1 schematically shows an appearance of an endoscope 100 to which the embodiments of the present invention is applicable.

The endoscope 100 includes a flexible tube 1 which is to be inserted in a human cavity. The proximal end of the flexible tube 1 is connected to the distal end portion (a lower end in FIG. 1) of an operation unit 2.

A tip of the flexible tube 1 is connected to a bendable portion 3, which can be bent at an arbitrary angle in an arbitrary direction with operation of a knob 4 provided to the operation unit 2. To the tip of the bendable portion 3, an optical unit 5 accommodating an objective optical system is connected.

To the tip of a flexible connecting tube 6 that is connected to an upper end portion of the operation unit 2, a connector 7 is provided. The connector 7 is to be connected to a video processor provided with a built-in light source unit (not shown) for supplying light to illuminate an object via the optical unit 5 and for processing image signals obtained through the optical unit 5.

Figure 2:
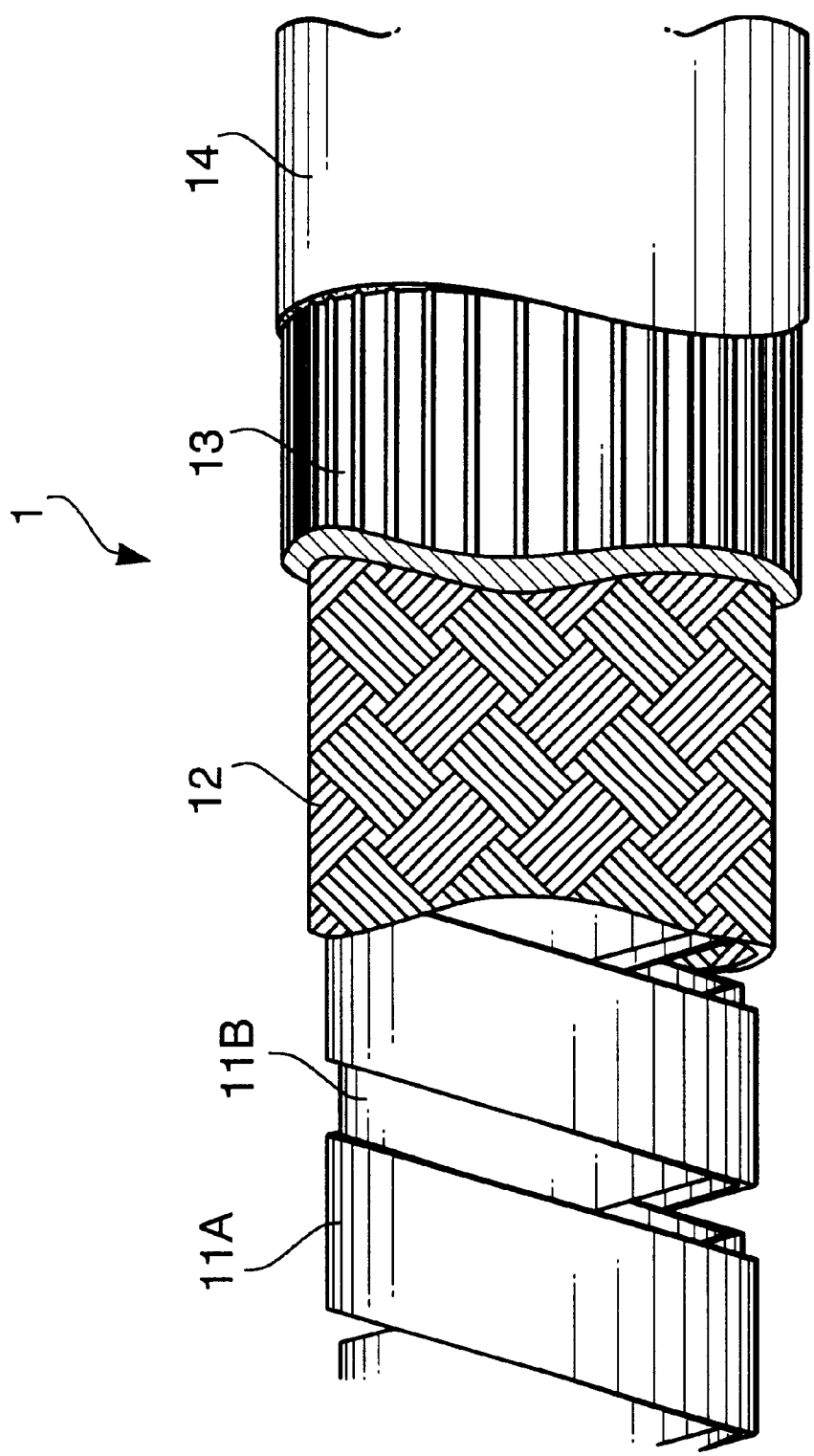
FIG. 2 shows a basic structure of a flexible tube.

FIG. 2 shows a basic structure of the flexible tube 1. The innermost layer of the flexible tube 1 is a spirally-wound tubes 11A and 11B. Each of the spirally-wound tubes 11A and 11B is formed by spirally winding belt-shaped metal such as stainless steel or copper alloy in a pitch (axial) direction of the tube. In this example, two spirally-wound tubes 11A and 11B whose winding directions are opposite are provided. The invention is not limited to the application to an endoscope having such a structure. The invention is applicable to an endoscope provided with a single spirally-wound tube or more than two spirally-wound tubes.

The spirally-wound tubes 11A and 11B is covered with a braided tube 12 which is formed with braided thin metal or non-metal wires. Further, the braided tube 12 is coated with a synthetic resin layer, or a flexible sheath 13 made of a synthetic resin. Further, the outer surface of the sheath 13 is covered with a coating layer 14.

The sheath 13 is made of, for example, material having polyurethane as the main ingredient. A pellet of the material is put in an extrusion molding device, and heat-melted material is directly applied onto the outer surface of the braided tube 12, and then cooled, so that a tubular sheath 13 is formed on the braided tube 12. The thickness of the sheath 13 is, for example, 0.3 through 0.8 mm (millimeter).

The coating layer 14 is formed of material having excellent resistance to chemicals, for example, acrylic, epoxy or urethane coating material. The coating layer 14 is coated on the outer surface of the sheath 13 at a thickness of 0.01 through 0.1 mm.

Figure 3:
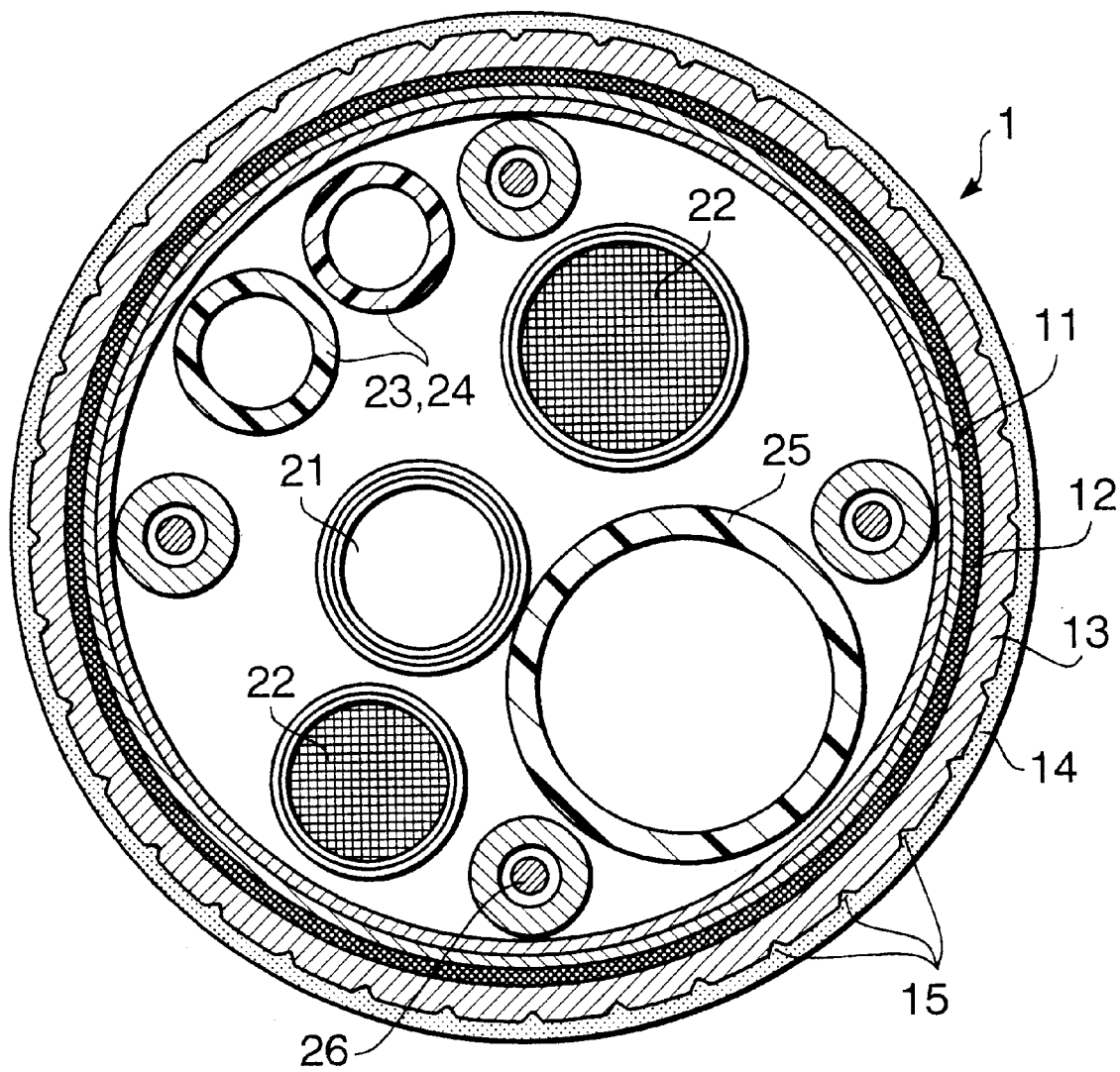
FIG. 3 is a cross sectional view of the flexible tube, taken along a plane perpendicular to an axis thereof, according to an embodiment of the invention.

FIG. 3 is a cross sectional view of the flexible tube 1, according to a first embodiment of the invention, along a plane perpendicular to the axis of the flexible tube 1.

In FIG. 3, numeral 21 denotes an image signal transmission cable, numeral 22 denotes an illumination light guide fiber bundle, numerals 23 and 24 denote air/water feeding tube, numeral 25 denotes a treatment accessory insertion channel, and numeral 26 denotes a bending operation wire.

On the outer circumferential surface of the sheath 13, V-shaped grooves 15, which extend in parallel with the axis of the flexible tube 1, are formed. In this embodiment, thirty-six (36) grooves 15, which are substantially evenly distributed in the circumferential direction of the sheath 13, are provided. A depth of each groove 15 is 0.01 through 0.05 mm.

Since the grooves 15 are formed on the outer surface of the sheath 13, a contacting area between the surface of the sheath 13 and the coating layer 14 increases. Further, the portions of the inner surface of the coating layer 14 facing the grooves 15 are protruded into the grooves 15, and accordingly, bonding force of the coating layer 14 with respect to the sheath 13 increases.

Since the coating layer 14 is hard to be peeled off from the sheath 13, the sheath 13 may not be exposed to outside and deteriorated by the disinfectant. Therefore, with the above-described structure, the flexible tube 1 has a higher resistance to the chemicals.

It should be noted that the cross sectional shape of the grooves may be some other shape. Further, the number of the grooves can be varied. Even a single groove may improve bonding force between the sheath 13 and the coating layer 14. Furthermore, the grooves need not extend in parallel with the axis of the sheath 13. For example, the grooves may be helically formed on the circumferential surface of the sheath 13.

Figure 4:
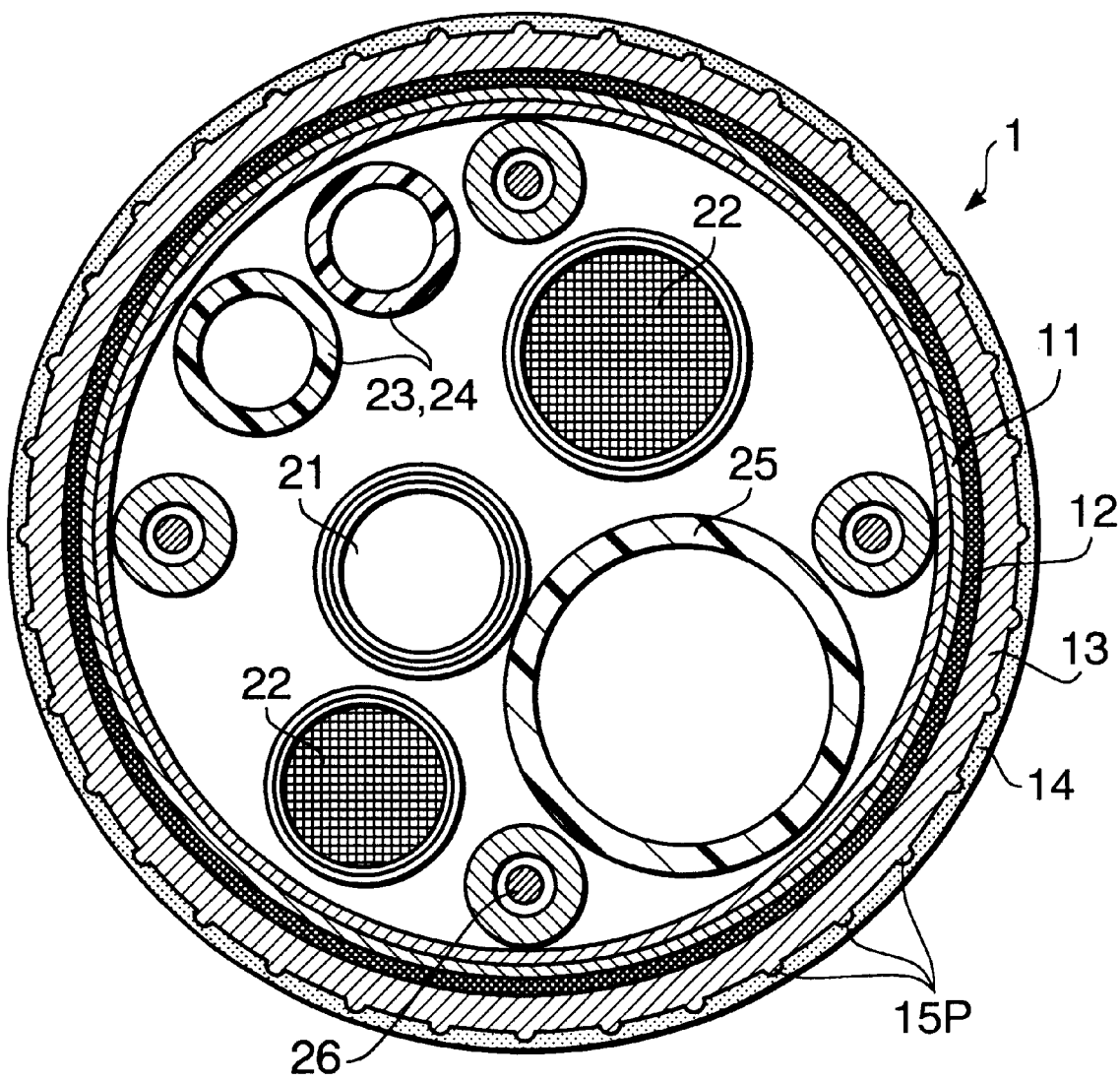
FIG. 4 is cross sectional view of the flexible tube, taken along a plane perpendicular to the axis thereof, according to a second embodiment of the invention.

FIG. 4 is a cross sectional view of the flexible tube, taken along a plane perpendicular to the axis thereof, according to a second embodiment of the invention.

In the second embodiment, instead of the V-shaped grooves, a plurality of protrusions 15P are formed on the circumferential surface of the sheath 13. The protrusions extend in a direction parallel with the axis of the sheath 13, and distributed over the circumferential surface of the sheath 13.

In this embodiment, a cross section of a protrusion 15P, taken along a plane perpendicular to the axis of the sheath 13, is semicircular. The height of the protrusion with respect to the surface of the sheath 13 should be lower than the thickness of the coating layer 14, and is, for example, 0.01 through 0.1 mm.

It should be noted that the shape of the protrusions is not limited to the described one, but various modification can also be applicable.

For example, the cross section of the protrusions 15P is not limited to the semicircle, and various shapes can be applicable. Further, the protrusions 15P need not be parallel with the axis of the sheath 13. The protrusions 15P may be formed helically on the circumferential surface of the sheath 13.

Furthermore, the number of the protrusions 15P is not limited. Even a single protrusion, the connection force between the coating layer 14 and the sheath 13 can be improved.

Still further, it is possible to provide both the grooves 15 and the protrusions 15P on the same circumferential surface of the sheath 13.

Furthermore, the grooves 15 or the protrusions 15P need not be formed as continuous lines over the entire length of the flexible tube 1, but can be provided intermittently.

The present invention is not limited to the application to the flexible tube 1. It can be applied to any other flexible part, such as a flexible connection tube 6 (see FIG. 1) of the endoscope 100.

As above, according to the present invention, bonding condition between the coating layer and the sheath is increased.

The present disclosure relates to the subject matter contained in Japanese Patent Application No. HEI 11-106291, filed on Apr. 14, 1999, which is expressly incorporated herein by reference in its entirety.

What is claimed is:

1. A flexible tube for an endoscope, having an outer tube member, a synthetic resin layer being formed on an outer circumferential surface of said outer tube member, a coating layer being formed on an outer circumferential surface of said synthetic resin layer, said outer circumferential surface of said synthetic resin layer being provided with at least one groove which extends substantially parallel with an axis of said outer tube member, and an inner surface of said coating layer contacting at least a portion of said at least one groove.

2. The flexible tube according to claim 1, wherein said at least one groove is provided over substantially an entire length of said flexible tube.

3. The flexible tube according to claim 1, wherein said at least one groove comprises a plurality of grooves.

4. The flexible tube according to claim 1, wherein said at least one groove is formed helically on said outer circumferential surface of said synthetic resin layer.

5. The flexible tube according to claim 1, wherein said inner surface of said coating layer is bonded to at least a portion of said at least one groove.

6. The flexible tube according to claim 1, wherein said coating layer is substantially resistant to chemicals.

7. The flexible tube according to claim 6, wherein the chemicals are disinfectants.

8. A flexible tube for an endoscope, having an outer tube member, a synthetic resin layer being formed on an outer circumferential surface of said outer tube member, a coating layer being formed on an outer circumferential surface of said synthetic resin layer, said outer circumferential surface of said synthetic resin layer being provided with at least one protrusion which extends substantially parallel with an axis of said outer tube member, and an inner surface of said coating layer contacting at least a portion of a region adjacent to said at least one protrusion.

9. The flexible tube according to claim 8, wherein said at least one protrusion is provided over substantially an entire length of said flexible tube.

10. The flexible tube according to claim 8, wherein said at least one protrusion comprises a plurality of protrusions.

11. The flexible tube according to claim 8, wherein said at least one protrusion is formed helically on said outer circumferential surface of said synthetic resin layer.

12. The flexible tube according to claim 8, wherein said inner surface of said coating layer is bonded to at least a portion of a region adjacent to said at least one protrusion.

13. The flexible tube according to claim 8, wherein said coating layer is substantially resistant to chemicals.

14. The flexible tube according to claim 13, wherein the chemicals are disinfectants.

15. A flexible tube for an endoscope, comprising:
   an outer tube member;
   a synthetic resin layer on an outer circumferential surface of said outer tube member, said synthetic resin layer having an outer circumferential surface;
   at least one groove and at least one protrusion on said outer circumferential surface of said synthetic resin layer, at least one of said at least one groove and said at least one protrusion extending substantially parallel with an axis of said outer tube member; and a coating layer on said outer circumferential surface of said synthetic resin layer, an inner surface of said coating layer contacting at least a portion of said at least one groove.

16. The flexible tube according to claim 15, wherein said inner surface of said coating layer is bonded to at least a portion of said at least one groove.

17. The flexible tube according to claim 15, wherein said coating layer is resistant to chemicals.

18. The flexible tube according to claim 17, wherein the chemicals are disinfectants.

19. A flexible tube for an endoscope, comprising:

an outer tube member;

a synthetic resin layer on an outer circumferential surface of said outer tube member, said synthetic resin layer having an outer circumferential surface;

at least one groove which extends substantially parallel with an axis of said outer tube member and positioned on said outer circumferential surface of said synthetic resin layer; and a coating layer on said outer circumferential surface of said synthetic resin layer, an inner surface of said coating layer protruding into said at least one groove.

20. The flexible tube according to claim 19, wherein said inner surface of said coating layer is bonded to at least a portion of said at least one groove.

21. The flexible tube according to claim 19, wherein said coating layer is substantially resistant to chemicals.

22. A flexible tube for an endoscope, having an outer tube member, a synthetic resin layer being formed on an outer circumferential surface of said outer tube member, a substantially disinfectant-resistant coating layer being formed on an outer circumferential surface of said synthetic resin layer, said outer circumferential surface of said synthetic resin layer being provided with at least one groove, and an inner surface of said coating layer contacting at least a portion of said at least one groove.

23. A flexible tube for an endoscope, having an outer tube member, a synthetic resin layer being formed on an outer circumferential surface of said outer tube member, a substantially disinfectant-resistant coating layer being formed on an outer circumferential surface of said synthetic resin layer, said outer circumferential surface of said synthetic resin layer being provided with at least one protrusion, and an inner surface of said coating layer contacting at least a portion of a region adjacent to said at least one protrusion.

24. A flexible tube for an endoscope, comprising:

an outer tube member;

a synthetic resin layer on an outer circumferential surface of said outer tube member, said synthetic resin layer having an outer circumferential surface;

at least one groove and at least one protrusion on said outer circumferential surface of said synthetic resin layer; and a substantially disinfectant-resistant coating layer on said outer circumferential surface of said synthetic resin layer, an inner surface of said coating layer contacting at least a portion of said at least one groove.

* * * * *